United States Patent [19]

Furukawa et al.

[11] Patent Number: 4,603,203
[45] Date of Patent: Jul. 29, 1986

[54] 3-AMINOPYRAZOLO[3,4-d]PYRIMIDINE DERIVATIVES AND PRODUCTION THEREOF

[75] Inventors: Yoshiyasu Furukawa, Takarazuka; Yoshitaka Maki, Kyoto, both of Japan

[73] Assignee: Takeda Chemical Industries, Ltd., Osaka, Japan

[21] Appl. No.: 678,479

[22] Filed: Dec. 5, 1984

[30] Foreign Application Priority Data

Dec. 14, 1983 [JP] Japan ................................ 58-237000
Jun. 18, 1984 [JP] Japan ................................ 59-125689

[51] Int. Cl.$^4$ .................. A61K 31/415; C07D 487/04
[52] U.S. Cl. ..................................... 544/262; 544/256
[58] Field of Search ................................ 544/256, 262

[56] References Cited

PUBLICATIONS

Naka Chemical and Pharmacalogical Bulletin 27(6) pp. 1328–1334, 1979.
Takeda–Derwent Abstract 32972 (9/1/76).

*Primary Examiner*—Donald G. Daus
*Assistant Examiner*—Robert Benson
*Attorney, Agent, or Firm*—Wegner & Bretschneider

[57] ABSTRACT

Novel 3-aminopyrazolo[3,4-d]pyrimidine derivatives represented by the general formula (I)

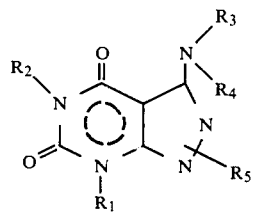

wherein $R_1$ and $R_2$ each represents an aliphatic hydrocarbon group; $R_3$ and $R_4$ each represents hydrogen, alkyl or acyl; $R_5$ is alkyl, alkoxycarbonyl or formyl; and the dotted line designates the presence of two double bonds on the pyrazole ring, to which $R_5$ is linked at either the 1- or 2-position and their salts, are useful for antiinflammatory, analgesic and antipyretic agents.

22 Claims, No Drawings

3-AMINOPYRAZOLO[3,4-d]PYRIMIDINE DERIVATIVES AND PRODUCTION THEREOF

The present invention relates to novel 3-aminopyrazolo[3,4-d]pyrimidine derivatives which are useful for pharmaceuticals and production thereof.

More specifically the present invention relates to novel 3-aminopyrazolo[3,4-d]pyrimidine derivatives represented by the general formula (I):

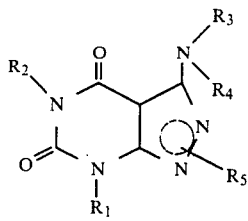

wherein $R_1$ and $R_2$ each represents an aliphatic hydrocarbon group; $R_3$ and $R_4$ each represents hydrogen, alkyl or acyl; $R_5$ is alkyl, alkoxycarbonyl or formyl; and the dotted line designates the presence of two double bonds on the pyrazole ring, to which $R_5$ is linked at either the 1- or 2- position and their salts. These compounds are useful for antiinflammatory, analgesic and antipyretic agents.

In the general formula [I], the aliphatic hydrocarbon group represented by $R_1$ and $R_2$ includes alkyl groups having 1 to 6 carbon atoms (e.g. methyl, ethyl, straight chained or branched propyl, butyl, pentyl, and hexyl) and alkenyl groups having 2 to about 6 carbon atoms (e.g. vinyl, allyl, 1-propenyl, isopropenyl, 2-butenyl, 2-pentenyl). Aliphatic hydrocarbon groups having 2 to 5 carbon atoms such as $C_{2-5}$ alkyl groups and $C_{2-5}$ alkenyl groups are preferable, and aliphatic hydrocarbon groups having 2 to 4 carbon atoms such as $C_{2-4}$ alkyl groups and $C_{2-4}$ alkenyl groups are especially preferred. Preferred examples of the alkyl group represented by $R_3$ or $R_4$, are alkyl group having 1 to 4 carbon atoms (e.g. methyl, ethyl, propyl, i-propyl, butyl, i-butyl) and preferred examples of the acyl group include alkanoyl groups, especially those of not more than 7 carbon atoms (e.g. acetyl, propionyl, butyryl, valeryl, cyclohexanecarbonyl), or the corresponding trifluoroalkylcarbonyl groups such as trifluoroacetyl or aromatic carbonyl groups (e.g. benzoyl).

Preferred examples of the alkyl group represented by $R_5$ are lower alkyl groups which may be substituted by halogen or hydroxyl group, and especially those having 1 to 4 carbon atoms. (e.g. methyl, ethyl, propyl, butyl, t-butyl). Examples of the alkoxycarbonyl group inlcude lower ($C_{1-4}$) alkoxycarbonyl groups and methoxycarbonyl and ethoxycarbonyl groups are particularly preferable.

Of the compounds represented by the above general formula [I], the compounds represented by the following formula (I') are especially preferred.

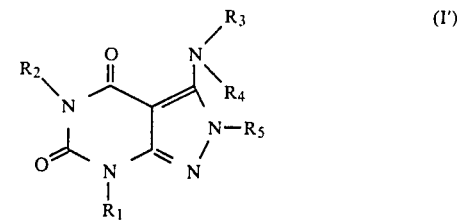

Wherein $R_1$ and $R_2$ each represents an aliphatic hydrocarbon group of 2 to 4 carbon atoms such as a $C_{2-4}$ alkyl group and a $C_{2-4}$ alkenyl group; $R_3$ and $R_4$ each represents hydrogen or alkyl; and $R_5$ is alkoxycarbonyl. The compounds of the formula (I') where $R_3$ is hydrogen, $R_4$ is hydrogen or methyl and $R_5$ is methoxycarbonyl or ethoxycarbonyl are especially preferred.

The preferred salts of the compound (I), are pharmaceutically acceptable salts, for example, inorganic acid salts siuch as hydrochlorides, hydrobromides, sulfates, nitrates, phosphates and organic acid salts such as acetates, tartrates, citrates, fumarates, maleates.

The compound represented by the general formula (I) can be produced for example, by the three processes shown below.

(a)

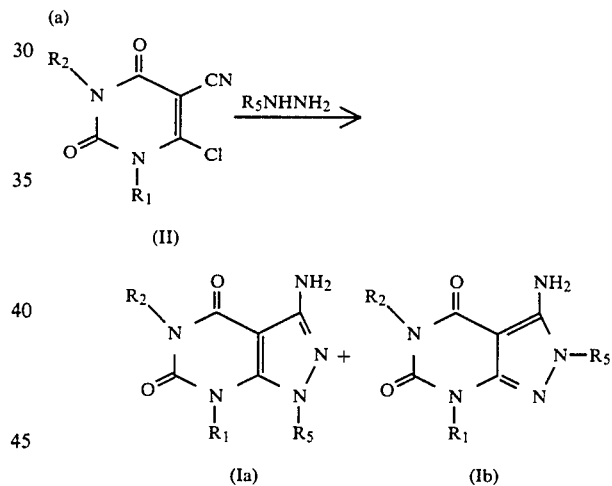

wherein $R_1$, $R_2$ and $R_5$ are as defined above.

(b)

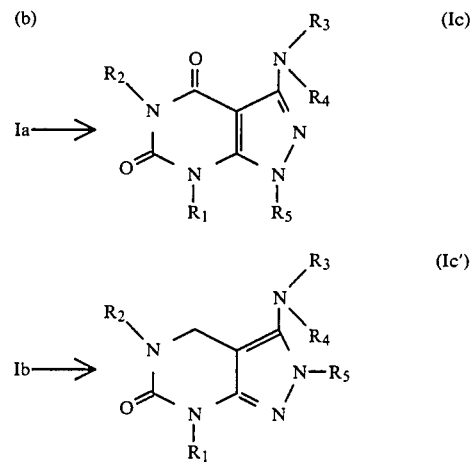

wherein each of symbols is as defined above, except the case in which $R_3$ and $R_4$ are both hydrogen.

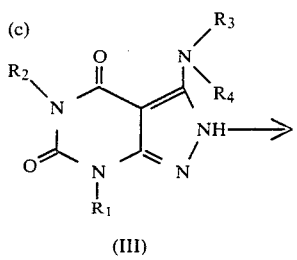

(III)

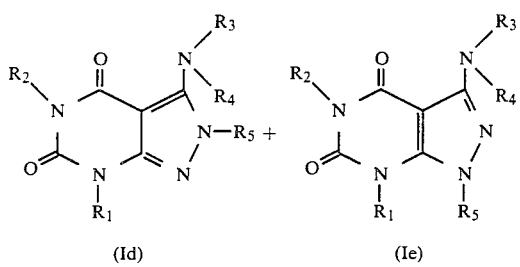

(Id)                    (Ie)

The reaction (a) above is desirably carried out with use of 2 to 5 moles of a substituted hydrazine per mole of the compound (II) in an alcohol such as methanol, ethanol, propanol and 2-methoxyethanol as solvent. The reaction is carried out advantageously at room temperature to 100° C. and for about 1 to 5 hours. The production ratio of (Ia) to (Ib) depends on the nature of $R_5$. Where $R_5$ is a methyl group, (Ia) is the predominant product, but the ratio of (Ib) produced increases with the bulkiness of $R_5$; in the case of $R_5$ being a t-butyl group, (Ib) is the predominant product. In cases where $R_5$ is an electron-attracting group such as a trifluoroethyl or alkoxycarbonyl group, (Ib) is also the predominant product. Separation of (Ia) from (Ib) is accomplished by conventional separating means such as silica gel chromatography. With reference to (II), the starting material for this reaction, the compound of (II) where $R_1$ and $R_2$ are methyl group, is a known compound [Chemical and Pharmaceutical Bulletin: 26, 3208 (1978)], and other compounds can also be synthesized according to the manner described in that reference.

The reaction (b) involves the alkylation or acylation of the compound (Ia) to yield the mono- or di-substituted product (Ic), wherein as the alkylating agent, there may be used alkyl halides, and as acylating agent, use is made of acid anhydrides and acid halides. These reagents are used in quantities within the range of 1 to 10 moles per mole of the compound (Ia) and are advantageously allowed to undergo reaction in the presence of an acid acceptor agent. Examples of the acid acceptor agent include potassium carbonate, sodium carbonate, triethylamine and pyridine, and the reaction is desirably carried out, in pyridine, dimethylformamide, dimethylacetamide or he like employed as a solvent, at room temperature to 100° C. for about 1 to 10 hours. The production rate of the mono- and di-substituted products depends on the type and amount of reagents, reaction temperature and time, etc., and bulky reagents easily yield the mono-substituted product.

The reaction (Ib)→(Ic') can be conducted in the same manner as that of the reaction (Ia)→(Ic).

The reaction (c) involves the replacement of the hydrogen in the pyrazole ring of the compound (III) with an alkyl, alkoxycarbonyl or formyl group to yield the desired compounds (Id) and (Ie). As alkylating agents, alkyl halides such as methyl iodide, ethyl iodide, propyl iodide, i-propyl iodide, butyl iodide and butyl bromide are available. For the purpose of introducing an alkoxycarbonyl group, methyl chlorocarbonate, ethyl chlorocarbonate, etc. are preferred. These reagents are used in quantities of 1 to 10 moles per mole of the starting material (III), and the reaction is preferably carried out in a solvent such as dimethylformanide, dimethylacetamide, dioxane and chloroform at room temperature to 50° C. for about 1 to 20 hours. As the acid acceptor, there may be employed potassium carbonate, sodium carbonate, triethylamine, etc., or pyridine may be used to function both as acid acceptor and solvent. As the formylating agent, a mixture of formic acid and acetic anhydride is used in excess to serve as solvent, and the reaction is preferably carried out at room temperature for 1 to 5 hours. In these reactions, in general the 2-substituted product (Id) is the predominant product, and where the 1-substituted product (Ie) is formed as a by-product, purification can be achieved by means such as silica gel chromatography. The starting material (III), which is used in these reactions, is produced by a known method [The Japanese Unexamined Patent Publication No. 31694/1974] or methods analogous thereto.

The compounds (III') of the formula (III), where $R_1$ and $R_2$ are different, are new and can be produced, for example, by the following procedure.

(d)

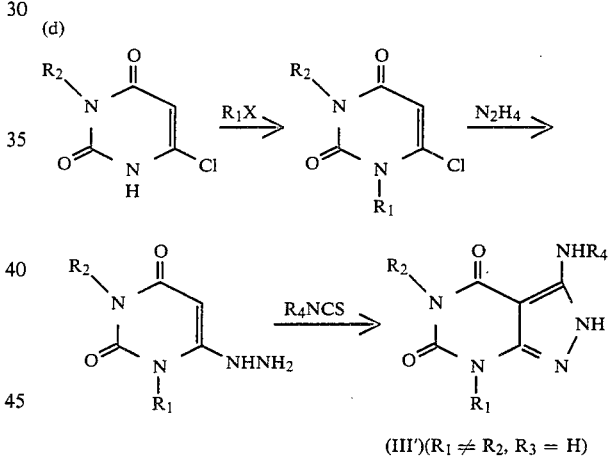

(III')($R_1 \neq R_2$, $R_3$ = H)

In these formulas $R_1$, $R_2$ and $R_4$ are as defined above and X is a halogen atom.

Salts of the compound (I) can be formed by the reaction for producing the compound (I), and can also be obtained by adding acid to the compound (I).

The 3-aminopyrazolo[3,4-d]pyrimidine derivatives of formula (I) and their salts in mammals exhibit antiinflammatory, analgesic and antipyretic actions, and are useful as an ameliorating and therapeutic agent for rheumatoid arthritis, low back pain or lumbago, shoulder-arm-neck syndrome or cervical syndrome, etc. When the compounds (I) are used as such drugs, they can be administered orally or parenterally as such or in admixture with suitable, pharmacologically acceptable carriers, excipients or diluents in such dosage form as powders, granules, tablets capsules, injections, suppositories and ointments. The dose of the compounds (I) varies with the kinds of disease, condition or symptom, subject, route of administration, etc. In the case of oral administration to adults with rheumathoid arthritis, for example, it is preferable to administer the compounds (I) in a single dose in the range of 0.1 to 20 mg/kg body weight, once to three times daily.

REFERENCE EXAMPLE 1

In 224 ml of phosphorus oxychloride was dissolved 61 g of diethylbarbituric acid, and 35 ml of dimethylformamide was added dropwise to the solution with stirring at room temperature. After the addition was completed, the reaction solution was refluxed for 3.5 hours. The reaction solution was concentrated to dryness under reduced pressure, and the remaining oily substance was added portionwise to ice-water. The crystals separated out were recovered by filtration to give 64 g of 6-chloro-1,3-diethyl-5-formyluracil melting at 88°–89° C.

50 g of this product and 50 g of hydroxylamine hydrochloride were stirred in 1 l of ethanol at room temperature for 30 minutes. 1 l of water was added to the reaction solution, and the precipitate was recovered by filtration to give 32.5 g of 6-chloro-1,3-diethyluracil-5-carbaldehyde oxime, m.p. 115°–116° C. 16 g of this product was dissolved in 320 ml of tetrahydrofurane, and 30 g of phosphorus oxychloride was added dropwise to the solution with stirring under ice-cooling, followed by stirring at room temperature for 1 hour. The reaction solution was concentrated to dryness under reduced pressure. 200 ml of diisopropyl ether was added to the residue; there separated out 12.4 of yellowish prisms of 6-chloro-5-cyano-1,3-diethyluracil melting at 92°–94° C.

| | Elemental analysis, for $C_9H_{10}N_3O_2Cl$ | | |
|---|---|---|---|
| | C (%) | H (%) | N (%) |
| Calcd. | 47.48 | 4.43 | 18.46 |
| Found | 47.29 | 4.31 | 18.35 |

According to the method described above, the following compounds were synthesized.

| $R_1$ | $R_2$ | M.P. (°C.) |
|---|---|---|
| $C_3H_7$ | $C_3H_7$ | 96–99 |
| i-$C_3H_7$ | i-$C_3H_7$ | 101–103 |
| $C_4H_9$ | $C_4H_9$ | 94–96 |

The intermediates (6-chloro-5-formyl and 6-chloro-5-cyano compounds) other than these compounds were difficult to crystallize, and therefore used without being purified in the subsequent reaction.

REFERENCE EXAMPLE 2

5 g of 6-chloro-5-cyano-1,3-diethyluracil and 2.2 ml of hydrazine monohydrate were stirred in 220 ml of methanol at room temperature for 10 minutes. The reaction solution was concentrated to dryness under reduced pressure, and the residue was recrystallized from aqueous methanol to give 4.3 g of colorless needles of 3-amino-5,7-diethylpyrazolo[3,4-d]pyrimidine 5,7(4H,6H)-dione melting at 246°–248° C. By the procedure described above, the following compounds were obtained.

| $R_1$ | $R_2$ | M.P. (°C.) |
|---|---|---|
| $C_3H_7$ | $C_3H_7$ | 227–229 |
| i-$C_3H_7$ | i-$C_3H_7$ | 291–295 |
| $C_4H_9$ | $C_4H_9$ | 192–194 |

REFERENCE EXAMPLE 3

In 50 ml of water was suspended 50 g of 1,3-dipropylbarbituric acid, and 500 ml of phosphorus oxychloride was added dropwise to the suspension with stirring under ice-cooling. The mixture was refluxed for 3 hours, and then concentrated to dryness under reduced pressure. The residue was poured into ice water, and the mixture was stirred; there separated out 44 g of yellow crystals of 6-chloro-1,3-dipropyluracil melting at 59°–63° C.

44 g of these crystals was suspended in 100 ml of ethanol, and 100 ml of hydrazine hydrate was added to the suspension, followed by stirring for 30 minutes. The reaction solution was concentrated to about a half of its original volume and allowed to cool; there separated out 34 g of yellow crystals of 6-hydrazino-1,3-dipropyluracil melting at 149°–151° C.

12 g of this product and 8.5 ml of methyl isothiocyanate were stirred in 100 ml of dimethylformamide at 100° to 110° C. for 12 hours. 10 ml of water was added to the reaction solution, and the mixture was allowed to cool; there separated out 5.8 g of brownish crystals of 3-methylamino-5.7-dipropylpyrazolo[3,4-d]-pyrimidine-4,6(5H,7H)-dione having a melting point higher than 300° C.

| | Elementary analysis, for $C_{12}H_{19}N_5O_2$ | | |
|---|---|---|---|
| | C (%) | H (%) | N (%) |
| Calcd. | 54.32 | 7.22 | 26.40 |
| Found | 54.47 | 7.26 | 26.50 |

In 60 ml of dichloromethane was suspended 4.52 g of 6-hydrazino-1,3-dipropyluracil and 3.9 g of phosgene iminium chloride was added portionwise to the suspension with stirring at room temperature, followed by stirring at room temperature for 1 hour. The reaction mixture was concentrated to dryness under reduced pressure, and the residue was recrystallized from aqueous alcohol to give 4.8 g of colorless crystals of 3-dimethylamino-5,7-dipropylpyrazolo[3,4-d]pyrimidine-4,6(5H,7H)-dione melting at 186°–188° C.

| | Elementary analysis for $C_{13}H_{21}N_5O_2$ | | |
|---|---|---|---|
| | C (%) | H (%) | N (%) |
| Calcd. | 55.90 | 7.56 | 25.07 |
| Found | 56.04 | 7.67 | 24.95 |

By the procedure described above, the following compounds were synthesized.

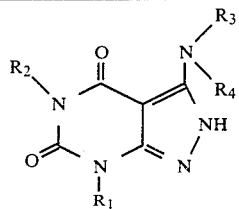

| Reference Example | R1 | R2 | R3 | R4 | M.P. (°C.) |
|---|---|---|---|---|---|
| 4 | C3H7 | C3H7 | H | C2H5 | 208–210 |
| 5 | C4H9 | C4H9 | H | C2H5 | 166–168 |
| 6 | C4H9 | C4H9 | CH3 | CH3 | 143–145 |
| 7 | C3H7 | C3H7 | H | COCH3 | 169–171 |
| 8 | C4H9 | C4H9 | H | COCH3 | 143–145 |
| 9 | i-C5H11 | i-C5H11 | H | CH3 | 244–246 |
| 10 | i-C5H11 | i-C5H11 | H | C2H5 | 122–124 |
| 11 | i-C5H11 | i-C5H11 | CH3 | CH3 | 159–161 |
| 12 | C5H11 | C5H11 | H | CH3 | 249–251 |

REFERENCE EXAMPLE 13

A mixture of 7 g of 6-chloro-3-propyluracil, 10.28 g of butyl bromide, 10.28 g of potassium carbonate, 6 g of potassium iodide and 80 ml of dimethylformamide was stirred at room temperature for 23 hours. After the reaction solution was concentrated to dryness under reduced pressure, 300 ml each of chloroform and water were added to the residue, and the mixture was shaken. The chloroform layer was washed with water and then concentrated to dryness under reduced pressure to give 6-chloro-1-butyl-3-propyluracil as a brown oily substance. This product, without being purified, was dissolved in 20 ml of ethanol, and 20 ml of 100% hydrazine hydrate was added to the solution, followed by stirring at room temperature for 1 hour. The reaction solution was concentrated to dryness under reduced pressure and the residue was washed with water and recrystallized from a mixture of ethanol, ethyl acetate and isopropyl ether to give 7 g of yellow prisms of 6-hydrazino-1-butyl-3-propyluracil melting at 146°–147° C.

| Elementary analysis, for $C_{11}H_{20}N_4O_2$ | | | |
|---|---|---|---|
| | C (%) | H (%) | N (%) |
| Calcd. | 54.98 | 8.39 | 23.31 |
| Found | 55.13 | 8.53 | 23.41 |

6.5 g of 6-hydrazino-1-butyl-3-propyluracil and 6.6 g of methyl isothiocyanate were stirred in 70 ml of dimethylformamide at 120° C. for 24 hours. Water and ethanol were added to the reaction solution, and the mixture was cooled. Yellowish crystals of 3-methylamino-7-butyl-5-propylpyrazolo[3,4-d]pyrimidine4,6(5H,7H)-dione, which separated out, were recovered by filtration.
Yield: 4.6 g, melting point: 284°–286° C.

| Elemental analysis, for $C_{13}H_{21}N_5O_2$ | | | |
|---|---|---|---|
| | C (%) | H (%) | N (%) |
| Calcd. | 55.90 | 7.58 | 25.07 |

-continued

| Elemental analysis, for $C_{13}H_{21}N_5O_2$ | | | |
|---|---|---|---|
| | C (%) | H (%) | N (%) |
| Found | 55.95 | 7.61 | 25.28 |

By the procedure described above, the following compounds were formed.

| Reference Example | R1 | R2 | R4 | M.P. (°C.) |
|---|---|---|---|---|
| 14 | C4H9 | C2H5 | CH3 | 289–292 |
| 15 | C2H5 | C4H9 | CH3 | 288–290 |
| 16 | C2H5 | C3H7 | CH3 | 291–294 |
| 17 | C3H7 | C4H9 | CH3 | 286–288 |
| 18 | CH2=CH—CH2 | C4H9 | CH3 | 280–282 |
| 19 | i-C3H7 | i-C3H7 | CH3 | 275–278 |
| 20 | i-C4H9 | i-C4H9 | CH3 | 290–300 |
| 21 | CH2=CH—CH2 | C3H7 | CH3 | 289–297 |

EXAMPLE 1

2.5 g of 6-chloro-5-cyano-1,3-diethyluracil and 1.1 g of methylhydrazine were stirred in 110 ml of methanol at room temperature for 1 hours. The reaction solution was concentrated to dryness under reduced pressure, and the residue was recrystallized from ethyl acetate/methanol to give 2.27 g of colorless needles of 3-amino-5,7-diethyl1-methylpyrazolo[3,4-d]-pyrimidine-4,6(5H,7H)-dione melting at 193°–194° C.

| Elemental analysis, for $C_{10}H_{15}N_5O_2$ | | | |
|---|---|---|---|
| | C (%) | H (%) | N (%) |
| Calcd. | 50.62 | 6.37 | 29.52 |
| Found | 50.53 | 6.11 | 29.39 |

EXAMPLES 2–3

By the method of Example 1, the following compounds were obtained.

| Example | R1 | R2 | M.P. (°C.) |
|---|---|---|---|
| 2 | C3H7 | C3H7 | 126–127 |
| 3 | C4H9 | C4H9 | 110–112 |

EXAMPLE 4

1.5 g of 6-chloro-5-cyano-1,3-diethyluracil and 0.9 of methoxycarbonylhydrazine were refluxed in 40 ml of methanol for 15 hours. The reaction solution was cooled, and there was obtained 1.33 g of colorless needles of 3-amino-5,7-diethyl-2-methoxycarbonyl-pyrazolo[3,4-d]pyrimidine-4,6(5H,7H)-dione melting at 209°–211° C.

| Elemental analysis for $C_{11}H_{15}N_5O_4$ | | | |
|---|---|---|---|
| | C (%) | H (%) | N (%) |
| Calcd. | 46.97 | 5.38 | 24.90 |
| Found | 46.79 | 5.36 | 24.81 |

EXAMPLES 5–8

According to the method of Example 4, the following compounds were obtained.

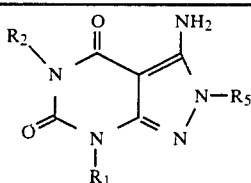

| Example | $R_1$ | $R_2$ | $R_5$ | M.P. (°C.) |
|---|---|---|---|---|
| 5 | $C_2H_5$ | $C_2H_5$ | $t$-$C_4H_9$ | 159–161 |
| 6 | $C_2H_5$ | $C_2H_5$ | $CH_2CF_3$ | 200–201 |
| 7 | $C_3H_7$ | $C_3H_7$ | $COOCH_3$ | 179–181 |
| 8 | $C_4H_9$ | $C_4H_9$ | $COOCH_3$ | 151–153 |

EXAMPLE 9

0.5 g of 6-chloro-5-cyano-1,3-diethyluracil and 0.35 g of β-hydroxyethylhydrazine were refluxed in 20 ml of methanol for 2 hours. The reaction solution was concentrated to dryness under reduced pressure, and the residue was chromatographed on 30 g of silica gel, followed by elution with chloroform. The first fraction was concentrated to dryness under reduced pressure, and the residue was recrystallized from methanol/ether to give 190 mg of colorless needles of 3-amino-5,7-diethyl-1-(β-hydroxyethyl)-pyrazolo[3,4-d]pyrimidine-4,6(5H,7H)-dione. Melting point: 150°–153° C.

| Elemental analysis for $C_{11}H_{17}N_5O_3$ | | | |
|---|---|---|---|
| | C (%) | H (%) | N (%) |
| Calcd. | 49.43 | 6.41 | 26.20 |
| Found | 49.21 | 6.63 | 25.94 |

The second fraction was concentrated to dryness under reduced pressure, and the residue was recrystallized from methanol to give 240 mg of colorless needles of 3-amino-5,7-diethyl-2-(β-hydroxyethyl)pyrazolo[3,4-d]pyrimidine-4,6(5H,7H)-dione melting at 206°–207° C.

| Elemental analysis for $C_{11}H_{17}N_5O_3$ | | | |
|---|---|---|---|
| | C (%) | H (%) | N (%) |
| Calcd. | 49.43 | 6.41 | 26.20 |
| Found | 48.82 | 6.42 | 25.76 |

EXAMPLES 10–12

According to the method of Example 9, the following compounds were obtained.

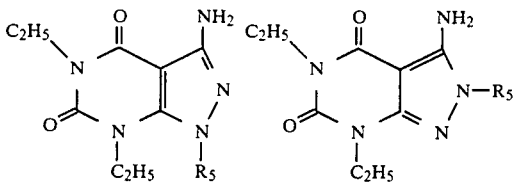

| Example | $R_5$ | M.P. (°C.) | M.P. (°C.) |
|---|---|---|---|
| 10 | $C_2H_5$ | 147–149 | 185–187 |
| 11 | $C_3H_7$ | 135–137 | 163–165 |
| 12 | $C_4H_9$ | 122–124 | 124–126 |

EXAMPLE 13

0.5 g of 3-amino-5.7-diethyl-1-methylpyrazolo[3,4-d]-pyrimidine-4,6(5H,7H)-dione and 0.9 g of acetic anhydride were stirred in 15 ml of pyridine at room temperature for 15 hours. The reaction solution was concentrated to dryness under reduced pressure, and the residue was recrystallized from chloroform/isopropyl ether to give 470 mg of yellowish needles of 3-acetylamino-5,7-diethyl-1-methylpyrazolo[3,4-d]pyrimidine-4,6(5H, 7H)-dione melting at 181°–182° C.

| Elemental analysis for $C_{12}H_{17}N_5O_3$ | | | |
|---|---|---|---|
| | C (%) | H (%) | N (%) |
| Calcd. | 51.60 | 6.14 | 25.08 |
| Found | 51.77 | 5.98 | 24.84 |

EXAMPLE –

In 20 ml of pyridine was dissolved under heating 0.7 g of 3-amino-5,7-diethyl-1-methylpyrazolo[3,4-d]pyrimidine-4,6(5H,7H)-dione, and 0.88 g of cyclohexanecarbonyl chloride was added to the solution, followed by stirring at 50° C. for 2 hours. The reaction was concentrated to dryness under reduced pressure, and after the residue was extracted with chloroform, the extract was chromatographed on 35 g of silica gel, followed by elution with chloroform. The main fractions were collected and concentrated to dryness under reduced pressure, and the residue was recrystallized from chloroform/isopropyl ether to give 0.64 g of colorless prisms of 3-cyclohexanecarbonylamino-5,7-diethyl-1-methylpyrazolo[3,4-d]pyrimidine-4,6(5H,7H)-dione melting at 165°–167° C.

| Elemental analysis for $C_{17}H_{25}N_5O_3$ | | | |
|---|---|---|---|
| | C (%) | H (%) | N (%) |
| Calcd. | 58.77 | 7.25 | 20.16 |
| Found | 58.83 | 7.32 | 19.56 |

EXAMPLES 15–22

According to the method of Example 13 or 14 the following compounds were synthesized.

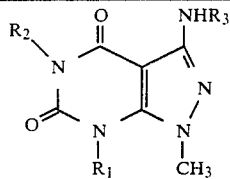

| Example | $R_1$ | $R_2$ | $R_3$ | M.P. (°C.) |
|---|---|---|---|---|
| 15 | $C_2H_5$ | $C_2H_5$ | $C_2H_5CO$ | 158–160 |
| 16 | $C_2H_5$ | $C_2H_5$ | $C_3H_7CO$ | 117–119 |
| 17 | $C_2H_5$ | $C_2H_5$ | $C_6H_5CO$ | 218–221 |
| 18 | $C_2H_5$ | $C_2H_5$ | $CF_3CO$ | 131–133 |
| 19 | $C_3H_7$ | $C_3H_7$ | $CH_3CO$ | 116–117 |
| 20 | $C_3H_7$ | $C_3H_7$ | $C_3H_7CO$ | 135–136 |
| 21 | $C_4H_9$ | $C_4H_9$ | $CH_3CO$ | 105–108 |
| 22 | $C_4H_9$ | $C_4H_9$ | $C_3H_7CO$ | 105–107 |

EXAMPLE 23

1 g of 3-amino-5,7-dibutyl-2-methoxycarbonyl-pyrazolo[3,4-d]pyrimidine-4,6(5H,7H)-dione, 690 mg of potassium carbonate and 0.3 ml of methyl iodide were stirred in 15 ml of dimethylformamide at room temperature for 6 hours. The reaction solution was concentrated to dryness under reduced pressure, and the residue was distributed between chloroform and water. The chloroform layer was concentrated to dryness under reduced pressure, and the residue was recrystallized from aqueous methanol to give 0.7 g of colorless prisms of 5,7-dibutyl-2-methoxycarbonyl-3-methylaminopyrazolo[3,4-d]pyrimidine-4,6-(5H,7H)-dione melting at 135°–136° C.

| Elemental analysis for $C_{16}H_{25}N_5O_4$ | | | |
|---|---|---|---|
| | C (%) | H (%) | N (%) |
| Calcd. | 54.69 | 7.17 | 19.93 |
| Found | 54.78 | 7.16 | 20.07 |

EXAMPLE 24

500 mg of 3-amino-5,7-diethyl-1-methylpyrazolo[3,4-d]-pyrimidine-4,6(5H,7H)-dione, 870 mg of potassium carbonate, 940 mg methyl iodide were stirred in 15 ml of dimethylacetamide at 70° C. for 5 hours. The reaction solution was concentrated to dryness under reduced pressure, and the residue was partitioned between chloroform and water. The chloroform layer was chromatographed on 35 g of silica gel, and elution was achieved with chloroform. The main fractions were collected and concentrated to dryness under pressure, and the residue was recrystallized from chloroform/isopropyl ether to give 260 mg of colorless prisms of 3-dimethylamino-5,7-diethyl-1-methylpyrazolo[3,4-d]pyrimidine-4,6-(5H,7H)-dione melting at 134° to 135° C.

| Elemental analysis for $C_{12}H_{19}N_5O_2$ | | | |
|---|---|---|---|
| | C (%) | H (%) | N (%) |
| Calcd. | 54.32 | 7.22 | 24.60 |
| Found | 54.04 | 7.34 | 26.29 |

EXAMPLE 25

1 g of 3-amino-5,7-diethyl-1-methylpyrazolo[3,4-d]-pyrimidine-4,6(5H,7H)-dione, 1.76 g of potassium carbonate and 2 g of ethyl iodide were reacted in 30 ml of dimethylacetamide at 70° C. for 5 hours. The reaction solution was treated in accordance with Example 24 to give 580 mg of colorless prisms of 3-ethylamino-5,7-diethyl-1-methylpyrazolo[3,4-d]pyrimidine-4,6(5H,7)-dione melting at 133°–135° C.

| Elemental analysis for $C_{12}H_{19}N_5O_2$ | | | |
|---|---|---|---|
| | C (%) | H (%) | N (%) |
| Calcd. | 54.32 | 7.22 | 26.40 |
| Found | 54.01 | 7.05 | 26.36 |

EXAMPLE 26

1,1 g of 3-ethylamino-5,7-diethylpyrazolo[3,4-d]pyrimidine-4,6(5H,7)-dione, 1 g of potassium carbonate and 1 ml of methyl iodide were stirred in 30 ml of dimethylacetamide at 40° C. for 4 hours. The reaction solution was partitioned between chloroform and water, and the chloroform layer was chromatographed on 30 g of silica gel, followed by elution with chloroform. The main fractions were collected and concentrated to dryness under reduced pressure, and the residue was recrystallized from acetone-hexane to give 0.7 g of colorless needles of 3-ethylamino-5,7-diethyl-2-methylpyrazolo[3,4-d]pyrimidine-4,6(5H,7H)-dione melting at 150°–152° C.

| Elemental analysis for $C_{12}H_{19}N_5O_2$ | | | |
|---|---|---|---|
| | C (%) | H (%) | N (%) |
| Calcd. | 54.32 | 7.22 | 26.40 |
| Found | 54.48 | 6.90 | 26.50 |

EXAMPLES 27–41

According to the manner in Example 26, the following compounds were synthesized.

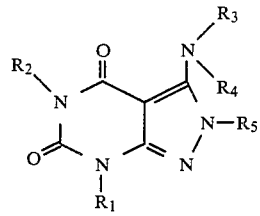

| Example | $R_1$ | $R_2$ | $R_3$ | $R_4$ | $R_5$ | M.P. (°C.) |
|---|---|---|---|---|---|---|
| 27 | $C_2H_5$ | $C_2H_5$ | H | $CH_3$ | $CH_3$ | 180–188 |
| 28 | $C_2H_5$ | $C_2H_5$ | H | $CH_3$ | $C_2H_5$ | 172–173 |
| 29 | $C_2H_5$ | $C_2H_5$ | H | $i-C_4H_9$ | $C_2H_5$ | 135–137 |
| 30 | $C_3H_7$ | $C_3H_7$ | H | $CH_3$ | $CH_3$ | 135–138 |
| 31 | $C_3H_7$ | $C_3H_7$ | H | $C_2H_5$ | $CH_3$ | 117–119 |
| 32 | $C_3H_7$ | $C_3H_7$ | $CH_3$ | $CH_3$ | $CH_3$ | 84–86 |
| 33 | $C_4H_9$ | $C_4H_9$ | H | $CH_3$ | $CH_3$ | 145–146 |
| 34 | $C_4H_9$ | $C_4H_9$ | H | $CH_3$ | $C_2H_5$ | 75–78 |
| 35 | $C_4H_9$ | $C_4H_9$ | H | $C_2H_5$ | $CH_3$ | 81–83 |
| 36 | $C_4H_9$ | $C_4H_9$ | $CH_3$ | $CH_3$ | $CH_3$ | 49–51 |
| 37 | $C_4H_9$ | $C_4H_9$ | H | $COCH_3$ | $CH_3$ | 180–182 |
| 38 | $C_4H_9$ | $C_4H_9$ | H | H | $CH_3$ | 132–134 |
| 39 | $i-C_5H_{11}$ | $i-C_5H_{11}$ | H | $CH_3$ | $CH_3$ | 105–110 |
| 40 | $C_5H_{11}$ | $C_5H_{11}$ | H | $CH_3$ | $CH_3$ | 120–121 |
| 41 | $C_4H_9$ | $C_2H_5$ | H | $CH_3$ | $CH_3$ | 130–132 |

EXAMPLE 42

In 35 ml of pyridine was dissolved 1.35 g of 3-methylamino-5,7-dipropylpyrazolo[3,4-d]pyrimidine-4,6(5H,7H)-dione, and 1 ml of ethyl chlorocarbonate was added to the solution, followed by stirring at room temperature overnight. The reaction solution was concentrated to dryness under reduced pressure, and the residue was partitioned between chloroform and water. The chloroform layer was chromatographed on 50 g of silica gel, and elution was effected with chloroform. The main fractions were collected and concentrated to dryness under reduced pressure, and the residue was recrystallized from aqueous ethanol to give 0.9 g of colorless needles of 2-ethoxycarbonyl-3-methylamino-5,7-dipropylpyrazolo[3,4-d]pyrimidine-4,6(5H,7H)-dione melting at 119°–121° C.

| Elemental analysis for $C_{15}H_{23}N_5O_4$ | | | |
|---|---|---|---|
| | C (%) | H (%) | N (%) |
| Calcd. | 53.40 | 6.87 | 20.76 |
| Found | 53.59 | 6.88 | 20.90 |

EXAMPLE 43

In 60 ml of dioxane was suspended 1.5 g of 5,7-diamyl-3-methylaminopyrazolo[3,4-d]pyrimidine-4,6(5H,7H)-dione and 2.7 g of triethylamine and 2.24 ml of methyl chlorocarbonate were added to the suspension, followed by stirring at 40° C. for 6 hours. The reaction solution was concentrated to dryness under reduced pressure, and the residue was partitioned between chloroform and water. The chloroform layer was chromatographed on 65 g of silica gel, and elution was effected with chloroform. The main fractions were collected and concentrated to dryness under reduced pressure, and the residue was recrystallized from aqueous ethanol to give 850 mg of colorless needles of 5,7-diamyl-2-methoxycarbonyl-3-methylaminopyrazolo[3,4-d]pyrimidine-4,6(5H,7H)-dione melting at 137°–139° C.

| Elemental analysis for $C_{18}H_{29}N_5O_4$ | | | |
|---|---|---|---|
| | C (%) | H (%) | N (%) |
| Calcd. | 56.98 | 7.70 | 18.46 |
| Found | 57.07 | 7.79 | 18.17 |

EXAMPLES 44–49

According to the method of Example 42 or 43, the following compounds were synthesized.

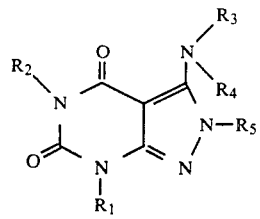

| Example | $R_1$ | $R_2$ | $R_3$ | $R_4$ | $R_5$ | M.P. (°C.) |
|---|---|---|---|---|---|---|
| 44 | $C_4H_9$ | $C_4H_9$ | H | $CH_3$ | $CO_2C_2H_5$ | 119–121 |
| 45 | $C_5H_{11}$ | $C_5H_{11}$ | H | $CH_3$ | $CO_2C_2H_5$ | 97–100 |
| 46 | $C_4H_9$ | $C_4H_9$ | H | H | $CO_2C_2H_5$ | 122–124 |
| 47 | $C_4H_9$ | $C_4H_9$ | $CH_3$ | $CH_3$ | $CO_2C_2H_5$ | 66–68 |
| 48 | $C_4H_9$ | $C_4H_9$ | $CH_3$ | $CH_3$ | $CO_2CH_3$ | 102–104 |
| 49 | $C_4H_9$ | $C_2H_5$ | H | $CH_3$ | $CO_2C_2H_5$ | 153–156 |

EXAMPLE 50

0.7 g of 3-ethylamino-5,7-dipropylpyrazolo[3,4-d]pyrimidine-4,6(5H,7H)-dione was stirred in 10 ml of a mixture of formic acid and acetic anhydride at 80° to 85° C. for 2 hours. The reaction solution was concentrated to dryness under reduced pressure, and the residue was chromatographed on 20 g of silica gel, followed by elution with chloroform. The main fractions were collected and concentrated to dryness under reduced pressure, and the residue was recrystallized from aqueous alcohol to give 0.58 g of colorless needles of 3-ethylamino-2-formyl-5,7-dipropylpyrazolo[3,4-d]pyrimidine-4,6(5H,7H)-dione melting at 114°–116° C.

| Elemental analysis for $C_{14}H_{21}N_5O_3$ | | | |
|---|---|---|---|
| | C (%) | H (%) | N (%) |
| Calcd. | 54.71 | 6.89 | 22.79 |
| Found | 54.71 | 6.97 | 22.91 |

EXAMPLES 51–53

According to the method of Example 50, the following compounds were synthesized.

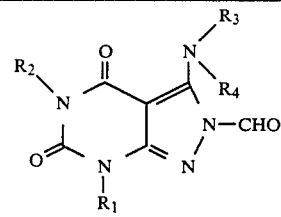

| Example | $R_1$ | $R_2$ | $R_3$ | $R_4$ | M.P. (°C.) |
|---|---|---|---|---|---|
| 51 | $C_3H_7$ | $C_3H_7$ | H | H | 139–141 |
| 52 | $C_4H_9$ | $C_4H_9$ | H | $CH_3$ | 130–312 |
| 53 | $C_4H_9$ | $C_4H_9$ | $CH_3$ | $CH_3$ | 69–71 |

EXAMPLE 54

In 130 ml of ethanol was dissolved 4 g of 3-amino-5,7-diethyl-1-methylpyrazolo[3,4-d]pyrimidine-4,6(5H,7H)-dione, and 15 ml of ethanol saturated with hydrogen chloride was added to the solution. The reaction was allowed to cool, whereby 2,7 g of colorless needles of 3-amino-5,7-diethyl-1-methylpyrazolo-[3,4-d]pyrimidine-4,6(5H,7H)-dione hydrochloride was obtained. Melting point 196°–196.5° C.

| Elemental analysis for $C_{10}H_{15}N_5O_2 \cdot HCl \cdot H_2O$ | | | |
|---|---|---|---|
| | C (%) | H (%) | N (%) |
| Calcd. | 41.18 | 6.22 | 24.01 |
| Found | 41.68 | 6.32 | 24.41 |

EXAMPLE 55

According to the method of Example 4, 3-amino-5,7-diisopropyl-2-methoxycarbonylpyrazolo[3,4-d]pyrimidine-4,6(5H,7H)-dione was synthesized. Melting point; 150°–151° C.

EXAMPLE 56

According to the method of Example 42, 2-ethoxycarbonyl-3-methylamino-5-butyl-7-ethylpyrazolo[3,4-d]pyrimidine-4,6(5H,7H)-dione was synthesized. Melting point; 177°–179° C.

EXAMPLE 57–67

According to the method of Example 43, the following compounds were synthesized.

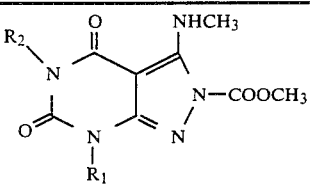

| Example | $R_1$ | $R_2$ | M.P. (°C.) |
|---|---|---|---|
| 57 | $C_4H_9$ | $C_4H_9$ | 129–130 |
| 58 | $C_3H_7$ | $C_3H_7$ | 159–160 |
| 59 | i-$C_4H_9$ | i-$C_4H_9$ | 184–185 |
| 60 | i-$C_3H_7$ | i-$C_3H_7$ | 183–184 |
| 61 | $C_4H_9$ | $C_2H_5$ | 130–132 |
| 62 | $C_2H_5$ | $C_4H_9$ | 197–199 |
| 63 | $C_2H_5$ | $C_3H_7$ | 203–205 |
| 64 | $C_4H_9$ | $C_3H_7$ | 136–138 |
| 65 | $C_3H_7$ | $C_4H_9$ | 135–136 |
| 66 | $CH_2=CH-CH_2-$ | $C_4H_9$ | 166–168 |
| 67 | $CH_2=CH-CH_2-$ | $C_3H_7$ | 165–167 |

Example of pharmaceutical preparation were the compound (I) of the present invention is used as a therapeutic agent for rheumatoid arthritis, shoulder-arm-neck syndrome, etc., it can be employed, for example, by a formulation as described in the following.

| 1. Tablet | |
|---|---|
| (1) 3-Butyrlamino-5,7-diethyl-1-methylpyrazolo[3,4-d]pyrimidine-4,6(5H, 7H)—dione | 10 mg |
| (2) Lactose | 35 mg |
| (3) Corn starch | 150 mg |
| (4) Microcrystalline cellulose | 30 mg |
| (5) Magnesium stearate | 5 mg |
| | 230 mg |

The whole amount of each of (1), (2) and (3), together with two thirds of the amount of (4) and a half of the amount of (5), are mixed and granulated. The residual amounts of (4) and (5) are added to the granules and compressed into a tablet.

| 2. Capsule | |
|---|---|
| (1) 5,7-Dibutyl-2-ethoxycarbonyl-3-methylaminopyrazolo[3,4-d]pyrimidine-4,6(5H,7H)—dione | 10 mg |
| (2) Lactose | 100 mg |
| (3) Microcrystalline cellulose | 70 mg |
| (4) Magnesium stearate | 10 mg |
| | 190 mg |

The whole amount each of (1), (2) and (3), together with a half of the amount of (4), are mixed and granulated. The residual amount of (4) is added to the granules, and the mixture is packed into a gelation capsule.

BIOLOGICAL EXPERIMENT

Experiment 1

Antiinflammatory action (Carrageenin edema method)

Using a group consisting of six Jcl:SD rats (6 weeks old, male), antiinflammatory action was investigated in accordance with the method of Winter et al. [Proc. Soc. Exp. Biol. Med., 111, 544 (1962)]. One hour after the oral administration of 50 mg/kg of a test sample, rats were injected subcutaneously with 0.05 ml of a 1% solution of carrageenin in physiological saline solution into a hind-paw. The volume of the hind-paw was measured 3 hours after, and before the injection of the carrageenin solution, and the edema volume was determined from the difference in the measurements. By comparing the edema volumes of animal groups untreated and treated with test samples, the inhibition rate was determined. The results are shown in Table 1.

Antiinflammatory action (Reversed passive Arthus reaction)

A group consisting of six Jcl:SD rats (7 weeks old, male) was used. Under ether anesthesia, the hair of the back was cut and 1 ml of a 0.5% solution of egg albumin in physiological saline solution was injected intravenously into the tail vein, followed by subcutaneous injection of 0.1 ml of rabbit anti-egg-albumin antiserum at each side of the left and right back and further subcutaneous injection on the left back of 0.1 ml of physiological saline solution. 3 hours later, the thickness of the individual skin spots was measured with a dial thickness guage to determine the degree of edema or swelling. The test sample in a dose of 20 mg/kg was intraperitoneally administered just before the injection of egg albumin. By comparing the edema volumes of animal groups non-treated and treated with test samples, swelling inhibition rate was determined.

The relationship between the edema inhibition rate and potency of antiinflammatory action in these two methods is described below.

| Edema inhibition rate (%) | Potency of antiinflammatory action |
|---|---|
| 0–9 | — |
| 10–19 | ± |
| 20–39 | + |
| 40–59 | ++ |
| >60 | +++ |

EXPERIMENT 2

Analgesic action (Phenylquinone writhing method)

Using a group consisting of 10 Slc:ICR mice (4 weeks old, male) analgesic action was investigated in accordance with the method of Sigmund et al. [Proc. Soc. Exp. Biol. Med., 95, 729 (1957)]. A test sample in a dose of 50 mg/kg was orally administered, and 30 minutes later, a 0.02% aqueous phenylquinone solution was intraperitoneally injected in the proportion of 0.1 ml per 10 g of body weight. Over the period of 20 minutes from the injection, the number of writhings was counted for the individual animals. By comparing the untreated and treated animal groups for the number of reactions, the writhing inhibition rate was determined. The results are shown in Table 1. Below indicated is the relationship between this inhibition rate and the potency of analgesic action.

| Writhing inhibition rate (%) | Potency of analgesic action |
|---|---|
| 0–29 | − |
| 30–49 | ± |
| 50–69 | + |
| 70–89 | + + |
| >90 | + + + |

TABLE 1

| Compound (I) | | | | $R_5$ (Position of substituent) | Antiinflammatory action | | Analgesic action |
|---|---|---|---|---|---|---|---|
| $R_1$ | $R_2$ | $R_3$ | $R_4$ | | Carrageenin | Arthus | |
| $C_2H_5$ | $C_2H_5$ | H | $C_3H_7CO$ | 1-$CH_3$ | +++ | ++ | + |
| $C_2H_5$ | $C_2H_5$ | H | H | 1-$C_4H_9$ | +++ | ++ | + |
| $C_2H_5$ | $C_2H_5$ | H | H | 2-$CO_2CH_3$ | +++ | +++ | ++ |
| $C_3H_7$ | $C_3H_7$ | $CH_3$ | $CH_3$ | 2-$CH_3$ | +++ | +++ | ++ |
| $C_3H_7$ | $C_3H_7$ | H | H | 2-CHO | +++ | +++ | +++ |
| $C_4H_9$ | $C_4H_9$ | H | $CH_3$ | 2-$CH_3$ | +++ | +++ | ++ |
| $C_4H_9$ | $C_4H_9$ | H | $CH_3$ | 2-$CO_2C_2H_5$ | ++ | +++ | ++ |
| $C_4H_9$ | $C_4H_9$ | $CH_3$ | $CH_3$ | 2-CHO | +++ | +++ | +++ |
| $C_4H_9$ | $C_4H_9$ | $CH_3$ | $CH_3$ | 2-$CH_3$ | +++ | +++ | + |
| $C_2H_5$ | $C_4H_9$ | H | $CH_3$ | 2-$CO_2CH_3$ | ++ | +++ | + |
| $C_4H_9$ | $C_3H_7$ | H | $CH_3$ | 2-$CO_2CH_3$ | +++ | +++ | ++ |
| $CH_2=CH-CH_2$ | $C_3H_7$ | H | $CH_3$ | 2-$CO_2CH_3$ | +++ | +++ | ++ |
| $C_3H_7$ | $C_3H_7$ | H | H | 2-$CO_2CH_3$ | +++ | +++ | +++ |
| $C_4H_9$ | $C_4H_9$ | H | $CH_3$ | 2-$CO_2CH_3$ | +++ | +++ | +++ |

What is claimed is:

1. A compound of the formula

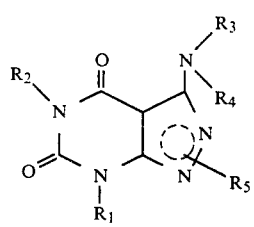

wherein $R_1$ and $R_2$ are $C_{1-6}$ alkyl or $C_{2-6}$ alkenyl; $R_3$ and $R_4$ are hydrogen, $C_{1-4}$ alkyl, $C_{1-6}$ alkyl-CO—, trifluoroacetyl or benzoyl, $R_5$ is $C_{1-4}$ alkyl which is optionally substituted with a halogen atom or a hydroxyl group, or $R_5$ is $C_{1-4}$ alkyl-O—CO—, the group $R_5$ being attached at the 1 or 2-position of the pyrazole ring; and wherein the dotted line designates the presence of two double bonds in the pyrazole ring; and the pharmaceutically acceptable salts thereof.

2. The compound according to claim 1 wherein $R_1$ and $R_2$ are $C_{2-5}$ alkyl group or $C_{2-5}$ alkenyl group.

3. The compound according to claim 1 wherein $R_5$ is $C_{1-4}$ alkyl—O—CO—.

4. The compound according to claim 3 wherein $R_1$ and $R_2$ are $C_{1-6}$ alkyl and $R_3$ and $R_4$ are $C_{1-4}$ alkyl.

5. The The compound according to claim 4 wherein $R_5$ is methoxycarbonyl.

6. The compound according to claim 5, wherein $R_1$ and $R_2$ are propyl and $R_3$ and $R_4$ are hydrogen.

7. The compound according to claim 5 wherein $R_1$ and $R_2$ are propyl, one of $R_3$ and $R_4$ is hydrogen and the other methyl.

8. The compound according to claim 1 wherein $R_5$ is $C_{1-14}$ alkyl.

9. The compound according to claim 8, $R_1$ and $R_2$ are $C_{1-6}$ alkyl group and $R_3$ and $R_4$ is hydrogen or $C_{1-4}$ alkyl.

10. The compound according to claim 9 wherein $R_5$ is methyl.

11. The compound according to claim 10 wherein $R_1$ and $R_2$ are propyl and $R_3$ and $R_4$ are methyl and $R_5$ is 2-methyl.

12. The compound according to claim 10 wherein $R_1$ and $R_2$ are butyl and one of $R_3$ and $R_4$ is hydrogen and the other is methyl and $R_5$ is 2-methyl.

13. The compound according to claim 10 wherein $R_1$ and $R_2$ are butyl, $R_3$ and $R_4$ are methyl and $R_5$ is methyl.

14. The compound according to claim 1 wherein $R_5$ is formyl.

15. The compound according to claim 14, $R_1$ and $R_2$ are propyl and $R_3$ and $R_4$ are methyl.

16. The compound according to claim 14 wherein $R_1$ and $R_2$ are butyl and $R_3$ and $R_4$ are methyl.

17. The compound according to claim 1 wherein $R_1$ is $C_{2-5}$ alkenyl, $R_2$ is $C_{1-6}$ alkyl, one of $R_3$ and $R_4$ is hydrogen and the other is $C_{1-4}$ alkyl and $R_5$ is methoxycarbonyl.

18. The compound according to claim 17 wherein $R_1$ is allyl, $R_2$ is propyl, $R_3$ is hydrogen, $R_4$ is methyl and $R_5$ is methoxycarbonyl.

19. The compound according to claim 1 wherein $R_1$ and $R_2$ are $C_{1-6}$ alkyl, one of $R_3$ and $R_4$ is hydrogen and the other is methyl and $R_5$ is 2-methoxycarbonyl.

20. The compound according to claim 19 where $R_1$ is butyl and $R_2$ is propyl.

21. The compound according to claim 19 wherein $R_1$ and $R_2$ are butyl.

22. The compound according to claim 19 wherein $R_1$ is ethyl and $R_2$ is butyl.

UNITED STATES PATENT AND TRADEMARK OFFICE
CERTIFICATE OF CORRECTION

PATENT NO. : 4,603,203

DATED : July 29, 1986

INVENTOR(S) : Furukawa et al.

It is certified that error appears in the above-identified patent and that said Letters Patent is hereby corrected as shown below:

In the abstract change

"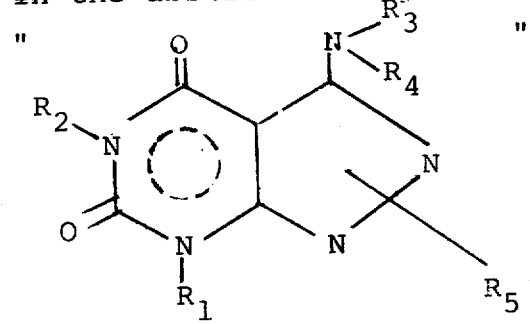"  to  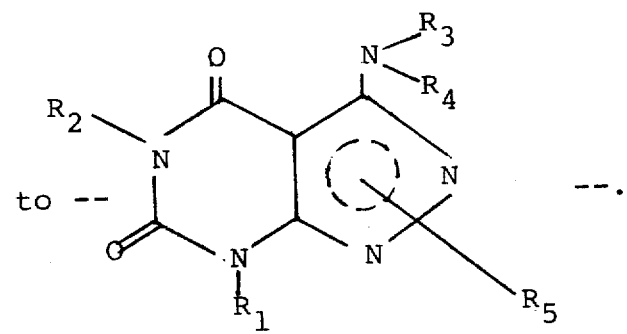 --.

In column 2, lines 59-67 change formula Ic' from

"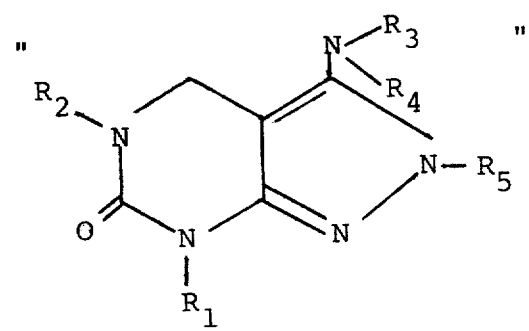"  to-- 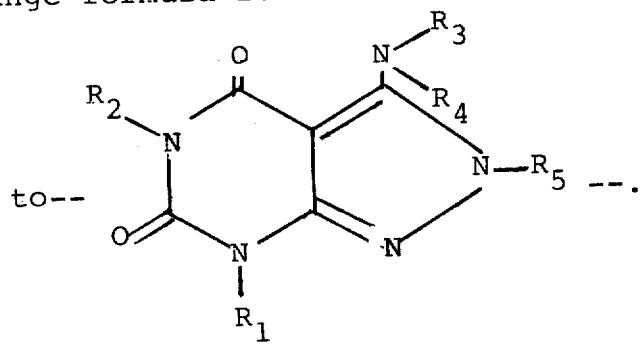 --.

UNITED STATES PATENT AND TRADEMARK OFFICE
CERTIFICATE OF CORRECTION

PATENT NO. : 4,603,203

DATED : July 29, 1986

INVENTOR(S) : Furukawa et al

Page 2 of 2

It is certified that error appears in the above-identified patent and that said Letters Patent is hereby corrected as shown below:

In column 10, line 38 after "EXAMPLE" delete "-" and insert -- 14 --.

Signed and Sealed this

Ninth Day of December, 1986

Attest:

DONALD J. QUIGG

Attesting Officer

Commissioner of Patents and Trademarks